United States Patent [19]

Tsuji et al.

[11] Patent Number: 5,591,985
[45] Date of Patent: Jan. 7, 1997

[54] SURFACE STATE INSPECTING SYSTEM INCLUDING A SCANNING OPTICAL SYSTEM FOR SCANNING A SURFACE TO BE INSPECTED WITH A FIRST LIGHT AND FOR SIMULTANEOUSLY SCANNING A DIFFRACTION GRATING WITH A SECOND LIGHT

[75] Inventors: Toshihiko Tsuji; Michio Kohno, both of Utsunomiya, Japan

[73] Assignee: Canon Kabushiki Kaisha, Tokyo, Japan

[21] Appl. No.: 374,884

[22] Filed: Jan. 19, 1995

[30] Foreign Application Priority Data

Jan. 21, 1994 [JP] Japan .................................. 6-005298

[51] Int. Cl.$^6$ ........................... G01N 21/88; G01N 21/89
[52] U.S. Cl. ................. 250/559.45; 250/559.48; 250/559.49; 250/559.41; 356/237
[58] Field of Search ................. 250/559.39, 559.40, 250/559.41, 559.42, 559.48, 559.49, 559.09, 578.1, 237.6, 225, 226; 356/237, 369

[56] References Cited

U.S. PATENT DOCUMENTS

| | | | |
|---|---|---|---|
| 4,412,743 | 11/1983 | Eberly | 356/237 |
| 4,795,911 | 1/1989 | Kohno et al. | 250/572 |
| 4,831,274 | 5/1989 | Kohno et al. | 250/563 |
| 4,886,975 | 12/1989 | Murakami et al. | 250/572 |
| 4,999,511 | 3/1991 | Kohno | 250/572 |
| 5,017,798 | 5/1991 | Murakami et al. | 250/572 |
| 5,105,092 | 4/1992 | Natsubori et al. | 250/572 |
| 5,245,403 | 9/1993 | Kato et al. | 356/237 |
| 5,365,067 | 11/1994 | Cole et al. | 250/341.8 |
| 5,461,474 | 10/1995 | Yoshii et al. | 356/237 |

FOREIGN PATENT DOCUMENTS

0567701  11/1993  European Pat. Off. .

*Primary Examiner*—Stephone Allen
*Attorney, Agent, or Firm*—Fitzpatrick, Cella, Harper & Scinto

[57] ABSTRACT

A surface state inspecting system includes a scanning optical system for scanning a surface to be inspected, with first light and simultaneously for scanning a diffraction grating with second light, wherein the first light and the second light have mutually different wavelengths and mutually different polarization directions, a light receiving optical system for receiving scattered light produced sidewardly from the surface and diffraction light produced sidewardly from the diffraction grating, and for superposing the received lights one upon another, and a photoelectric converting device for converting light from the light receiving optical system into an electric signal, wherein the scanning optical system and the light receiving optical system provide an optical system which is telecentric with respect to the surface to be inspected.

8 Claims, 6 Drawing Sheets

SURFACE STATE INSPECTING SYSTEM INCLUDING A SCANNING OPTICAL SYSTEM FOR SCANNING A SURFACE TO BE INSPECTED WITH A FIRST LIGHT AND FOR SIMULTANEOUSLY SCANNING A DIFFRACTION GRATING WITH A SECOND LIGHT

FIELD OF THE INVENTION AND RELATED ART

This invention relates to a surface state inspecting system. In another aspect, the invention is concerned with an exposure apparatus having such a surface state inspecting system or with a device manufacturing method for manufacturing devices by using such an apparatus.

There are surface state inspecting systems for inspecting a foreign particle such as a scratch, for example, on a reticle (photomask), which include a scanning optical system for scanning the surface of the reticle with a laser beam, and a light receiving optical system for receiving light, of scattered light from the reticle being scanned, which is scattered sidewardly with respect to an optical axis (direction) of the scanning optical system.

In such a surface state inspecting system, however, the light receiving system may receive a portion of diffraction light or scattered light from a circuit pattern on the reticle, and thus, there is a possibility of erroneously detecting the circuit pattern on the reticle as a foreign particle. Also, because the light receiving system is disposed aside, depending on the closeness or farawayness of the position of deposition of the particle to or from the light receiving optical system, the cubic angle with respect to the light receiving optical system changes. Therefore, even with the same size particle, the quantity of scattered light entering the light receiving optical system may change.

SUMMARY OF THE INVENTION

It is accordingly a first object of the present invention to provide a surface state inspecting system by which erroneous detection of a circuit pattern as a foreign particle is prevented and by which the particle detection is performed at a substantially constant sensitivity regardless of the position of deposition of the particle.

In accordance with a first aspect of the present invention, to achieve the first object, there may be provided a surface state inspecting system, comprising: a scanning optical system for scanning a surface to be inspected, with first light and simultaneously for scanning a diffraction grating with second light, wherein the first light and the second light have mutually different wavelengths and mutually different polarization directions; a light receiving optical system for receiving scattered light produced sidewardly from the surface and diffraction light produced sidewardly from the diffraction grating, and for superposing the received lights one upon another; and photoelectric converting means for converting light from said light receiving optical system into an electric signal; wherein said scanning optical system and said light receiving optical system provide an optical system which is telecentric with respect to the surface to be inspected.

Any particle can be detected on the basis of a beat signal based on heterodyne interference between the scattered light and the diffraction light which signal is obtainable from the photoelectric converting means. Therefore, erroneous detection of a circuit pattern as a foreign particle is avoided. Additionally, since the scanning optical system and the light receiving optical system provide an optical system which is telecentric with respect to the surface to be inspected, particle detection is performed at a substantially constant sensitivity and substantially constant precision regardless of the position of deposition of the particle.

It is a second object of the present invention to provide a surface state inspecting system by which particle detection is performed at a more constant sensitivity. To this end, said photoelectric converting means may have a light receiving surface which may be disposed at one of (i) a position of an aperture stop of said light receiving optical system and (ii) a position optically conjugate with the position of the aperture stop of said light receiving optical system.

With this arrangement, during the scan, scattered light from different points on the surface being inspected and diffraction light from different points on the diffraction grating are projected on a fixed position on the light receiving surface of the light receiving optical system. Thus, the stability of sensitivity is improved.

It is a third object of the present invention to provide a surface state inspecting system by which an adverse effect of scattered light from a surface other than the surface to be inspected is reduced. To this end, said light receiving optical system may include a field stop disposed at a position optically conjugate with the surface to be inspected.

With this arrangement, the quantity of scattered light from a surface other than the surface to be inspected and entering the photoelectric converting means is reduced by the field stop. Thus, erroneous detection of a pattern or a particle on a surface other than the surface to be inspected, is avoided.

It is a fourth object of the present invention to provide a surface state inspecting system by which adverse effects of scattered light from a surface other than the surface to be inspected, is further reduced. To this end, said field stop may be disposed with inclination so that it is placed along an imaging plane which satisfies a scheimpflug's condition with the surface to be inspected.

With this arrangement, the quantity of scattered light from a surface other than the surface to be inspected and entering the photoelectric converting means is reduced largely, such that erroneous detection of a pattern or a particle on a surface other than the surface to be inspected, is avoided more effectively.

It is a fifth object of the present invention to provide a surface state inspecting system by which a beat signal is produced with a stable signal-to-noise (S/N) ratio, through a simple optical arrangement, and also by which an adverse effect of scattered light from a surface other than the surface to be inspected is reduced. To this end, said light receiving optical system may further include a first lens, an aperture stop, a second lens and a field stop disposed in the named order from the surface to be inspected and the diffraction grating, wherein said aperture stop may be disposed adjacent to a focal point position of said first lens, wherein said field stop may be disposed at an imaging position of the surface to be inspected, as defined by said first and second lenses, and wherein said photoelectric converting means may have its light receiving surface disposed at the position of said aperture stop or at a position optically conjugate with the position of said aperture stop.

With this arrangement, the quantity of scattered light from a surface other than the surface to be inspected and entering the photoelectric converting means is reduced, such that erroneous detection of a pattern or a particle on a surface other than the surface to be inspected, is avoided. Also, during the scan, scattered light from different points on the surface being inspected and diffraction light from different points on the diffraction grating are projected on a fixed position on the light receiving surface of the photoelectric converting means. Thus, the S/N ratio of the beat signal is stabilized.

It is a sixth object of the present invention to provide a surface state inspecting system by which a surface to be inspected and a diffraction grating can be scanned simultaneously with different lights. To this end, said scanning optical system may include (i) supplying means for supplying the first and second lights in a state in which the first and second lights are superposed one upon another, (ii) a scanning mirror for scanningly deflecting the superposed first and second lights, (iii) a scanning lens for collecting the first and second lights from said scanning mirror to the surface to be inspected and to the diffraction grating, and (iv) a beam splitter for defining, for the first light, a first light path to the surface to be inspected and for defining, for the second light, a second light path to the diffraction grating.

With this arrangement, a common optical member is used for scanning and collecting the first and second lights and, therefore, the structure of the scanning optical system is made simple.

It is a seventh object of the present invention to provide an exposure apparatus having a surface state inspecting system by which erroneous detection of a circuit pattern as a foreign particle is avoided and by which particle detection is performed at a substantially constant sensitivity regardless of the position of deposition of the particle.

An exposure apparatus according to this aspect of the present invention is provided with any one of the surface inspecting systems described hereinbefore, such that the presence or absence of a particle on a reticle is detected correctly. Thus, only a reticle having no deposition of a particle is used for the exposure process, whereby the reliability is improved.

It is an eighth object of the present invention to provide a device manufacturing method for manufacturing microdevices such as ICs, LSIs, magnetic heads, liquid crystal panels or CCDs, for example, by using an exposure apparatus equipped with a surface state inspecting system by which erroneous detection of a circuit pattern as a foreign particle is avoided and by which particle detection is performed at substantially constant sensitivity regardless of the position of deposition of the particle.

In accordance with this aspect of the present invention, the device manufacturing method includes detecting the presence or absence of a particle on a reticle by using any one of the surface state inspecting systems as described hereinbefore. With this method, the presence or absence of a particle on a reticle is detected correctly, and a device pattern of such a reticle as having no deposition of a particle is printed on a substrate. Thus, a device with improved accuracy is produced.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Figure 1:
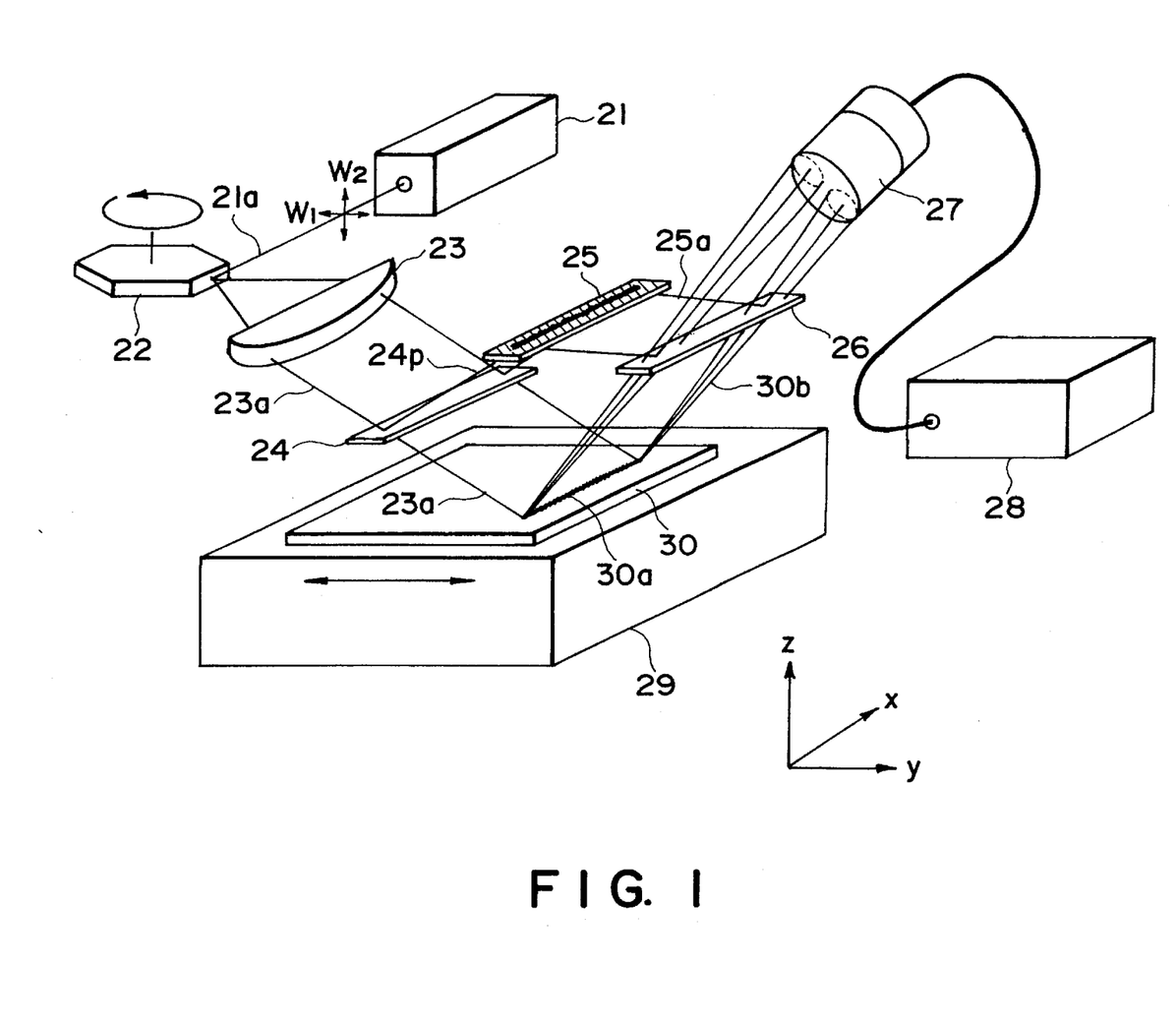
FIG. 1 is a schematic view of a surface state inspecting system according to an embodiment of the present invention.
Figure 2:
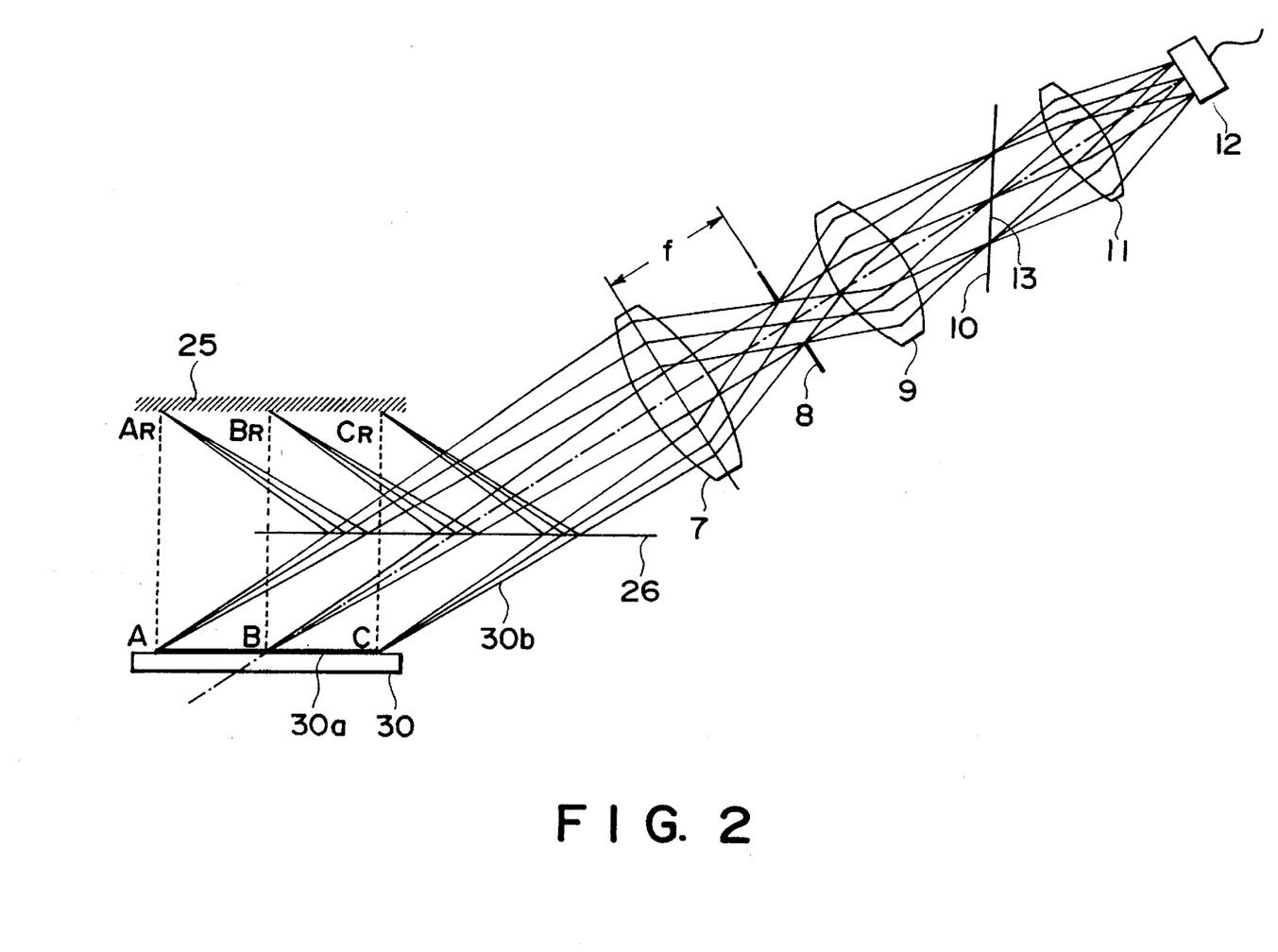
FIG. 2 is a schematic view of a light receiving system of the surface state inspecting system of FIG. 1.

FIGS. 1 and 2 show a surface state inspecting system according to an embodiment of the present invention. FIG. 1 is a schematic view of a general structure of the surface state inspecting system, and FIG. 2 illustrates a light receiving system of the surface state inspecting system. The surface state inspecting system of this embodiment comprises a laser light scan type particle inspecting system wherein scattered light produced sidewardly from a particle is detected as a beat signal on the basis of heterodyne interference such that it is discriminated from a signal provided by scattered light produced from a portion other than the particle. A basic concept of such a surface state detecting system for particle detection based on heterodyne interference is disclosed in Published European Patent Application No. 567701, published Jun. 16, 1993, the application being filed in the name of the assignee of the subject application.

In FIG. 1, denoted at 21 is a dual frequency laser light source means for supplying a pair of laser beams having mutually different wavelengths (w1 and w2) and having mutually orthogonal polarization directions, these laser beams being supplied in the form of parallel light and in the state in which the laser beams are superposed one upon another. Denoted at 22 is a rotatable mirror such as a polygonal mirror or a galvano mirror, for example, and denoted at 23 is an f-θ lens system. Denoted at 24 is a wave divider such as a polarization beam splitter, for example, and denoted at 25 is a diffraction grating. Denoted at 26 is a wave combining device such as a beam splitter, for example, and denoted at 27 is a light receiving optical system. Denoted at 28 is a signal processing system, and denoted at 29 is a stage. Denoted at 30 is a reticle. The diffraction grating has grating elements disposed with inclination with respect to the scan direction, and it serves to reflectively diffract input light sidewardly to produce a plurality of diffraction lights. In this embodiment, of these diffraction light produced sidewardly, diffraction light of a particular order or orders is used for the heterodyne interference.

Details of the structure of the dual frequency laser light source means 21 are disclosed in the aforementioned Published European patent application. It is a possible alternative that a Zeeman laser adapted to directly emit linearly polarized lights of different wavelengths and different polarization directions may be used as the dual frequency laser light source means 21, with simplification of the illumination system.

A pair of linearly polarized lights 21a from the dual frequency laser light source means 21 are projected on the rotatable mirror 22. The rotatable mirror 22 reflectively deflects the paired linearly polarized lights, being mutually superposed, and directs them to the f-θ (scanning) lens 23 and the wave divider 24. By means of the wave divider 24, the paired linearly polarized lights being mutually superposed are separated from each other, such that linearly polarized light 24s is projected on the surface of the reticle 30 on which a circuit pattern is formed, while linearly polarized light 24p is projected on the diffraction grating 25. This diffraction grating 25 is provided to produce reference light. The f-θ lens 23 is arranged so that the linearly polarized lights 24s and 24p are converged or collected upon the reticle 30 and the diffraction grating 25, respectively. Additionally, it is arranged to provide a telecentric optical system on the reticle 30 side (the side at the surface to be inspected) such that all the lights impinging on different points on the reticle 30 and the diffraction grating 25 are parallel to the optical axis of the f-θ lens 23. With rotation of the rotatable mirror 36, the linearly polarized lights 24s and 24p scan the reticle 30 and the diffraction grating 25, respectively, in the X direction. By this, on the surface of the reticle 30 to be inspected, for example, a scan line 30a is defined. On the or her hand, the reticle 30 is moved in the Y direction such that, with the scan (displacement) of the linearly polarized light $L_V$ in the X direction and the movement of the reticle 30 in the Y direction, the entire surface of the reticle 30 to be inspected can be illuminated with the linearly polarized light 24s.

In the surface state inspecting system of this embodiment, the linearly polarized lights 24s and 24p having different wavelengths and having different polarization directions are supplied while they are superposed one upon another (as depicted at 21a). Also, common optical members 22, 23 and 24 are used for scanning and collecting the linearly polarized lights 24s and 24p. With this arrangement, the structure of the scanning means is made very simple.

Referring to FIG. 2, the light receiving system of the surface state inspecting system of this embodiment will be explained.

In FIG. 2, a partial reflecting mirror (half mirror) 26 serves to combine scattered light 30b produced sidewardly from a particle on the reticle 30 and diffraction light 25a produced sidewardly from the diffraction grating 25, both being produced in response to scanning of the reticle 30 and the diffraction grating 25 with the linearly polarized lights 24s and 24p, respectively. Namely, it serves to transmit the scattered light from the particle on the reticle 30 and to reflect the diffraction light from the diffraction grating 25, to thereby superpose them one upon another, the thus superposed lights being directed to a light receiving lens 7. An aperture stop 8 is disposed at a rear focal point position of the light receiving tens 7, such that on the reticle 6 (diffraction grating 25) side the light receiving system is telecentric. Thus, the light receiving lens 7 serves to converge or collect, to the center of the aperture of the stop 8, those scattered lights (central rays) emanating from points A, B and C on the reticle 30 parallel to the optical axis of the light receiving lens 7 as well as those diffraction lights (central rays) emanating from points $A_R$, $B_R$ and $C_R$ on the diffraction grating 25 parallel to the optical axis of the light receiving lens. The scattered light and diffraction light passing through the aperture stop 8 goes through a field stop 10 and a lens 11, and is received by a photodetector 12. In response, the photodetector outputs a beat signal produced as a result of heterodyne interference between the scattered light and the diffraction light of the same polarization direction, and this signal is applied to the signal processing system 28 of FIG. 1. The signal processing system compares the intensity of or the time moment of generation of this beat signal, for example, each with a corresponding threshold. If the threshold is exceeded, then presence of a particle is concluded.

The scattered light 30b produced sidewardly from a particle on the reticle 30 contains the same polarization component as that of the diffraction light 25a produced sidewardly from the diffraction grating 25. On the other hand, scattered light or diffraction light produced sidewardly from a circuit pattern of the reticle 30 does not contain the same polarization component as that of the diffraction light 25a produced sidewardly from the diffraction grating 25, and thus, such scattered light or diffraction light does not cause heterodyne interference. Therefore, with the surface state inspecting system according to the present embodiment, erroneous detection of a circuit pattern as a foreign particle is prevented.

Further, owing to the use of a telecentric light receiving system on the side of the reticle 30 and the diffraction grating 25, the light receiving lens 7 is able to receive scattered light 30b from the reticle 30 with a constant receiving angle and cubic angle as well as diffraction light (reference light) from the diffraction grating with a constant receiving angle and cubic angle. As a result, for the same size particle, a constant intensity of scattered light enters the light receiving lens 7 (aperture stop 8) regardless of the position of deposition of the particle on the reticle 30. Additionally, it is accurately superposed one upon another with the diffraction light 25a from the diffraction grating 25. Therefore, the beat signal from the photodetector 12 has a constant intensity. Thus, the particle detection is performed at a substantially constant sensitivity, regardless of the position of deposition of the particle.

Also, because of the use of a scanning optical system which is telecentric on the side of the reticle 30 and the diffraction grating 25, as has been explained with reference to FIG. 1, the incidence angle of the illumination light (linearly polarized lights 24s and 24p) irradiating different points on the reticle 30 and the diffraction grating 25 is maintained constant such that, with respect to these points, the inspection is performed under the same conditions. Thus, the particle detection is performed at substantially constant precision regardless of the position of deposition of the particle.

The field stop 10 is provided at the imaging position 13 where an image of the surface (to be inspected) of the reticle 30 is formed through the lenses 7 and 9. The field stop 10 is disposed with inclination with respect to the optical axis of the light receiving system, and is placed along the imaging plane satisfying the scheimpflug's condition with the surface of the reticle 30. The provision of a field stop in this manner effectively prevents incidence, on the photodetector 12, of scattered light or diffraction light from a surface other than the surface of the reticle 30.

On the other hand, the photodetector 12 has a light receiving surface which is disposed at the imaging position of the aperture stop 8 by the lenses 9 and 11. The provision of a photodetector (photoelectric converting means) in this manner is effective to assure that scattered lights from different points on the surface of the reticle 30 as well as diffraction lights from different points on the diffraction grating 25 are projected at a fixed point on the light receiving surface of the photodetector, whereby the sensitivity is stabilized.

In order to obtain a beat signal of good contrast from the photodetector 12, the optical path length between the light receiving lens 7 and the reticle 30 may preferably be made approximately equal to the optical path length between the light receiving lens 7 and the diffraction grating 25, such that the reticle 30 and the diffraction grating 25 may be disposed at substantially optically equivalent positions.

Figure 3:
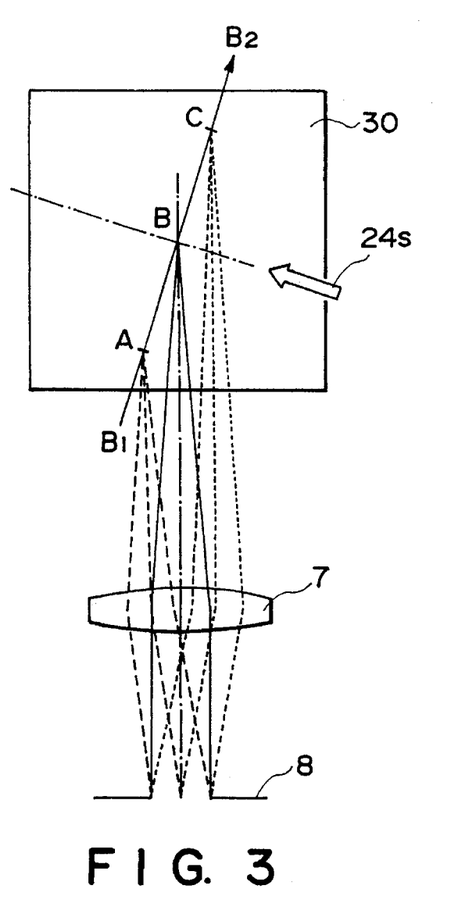
FIG. 3 is a schematic view of a modified form of the surface state inspecting system as shown in FIGS. 1 and 2.

FIG. 3 is a schematic view of a modified form of the surface state inspecting system of FIGS. 1 and 2. In the surface state inspecting system shown in FIGS. 1 and 2, the optical axis is laid within a plane which contains the scanning direction and which is perpendicular to the surface of the reticle 6. In this example, however, as shown in FIG. 3, the optical axis of the light receiving system is placed in a direction twisted relative to the scanning direction $B_1$–$B_2$ so that the light receiving system receives such light as scattered sidewardly and slightly backwardly. This makes it more difficult for diffraction light from a circuit pattern of the reticle 30 to be received by the light receiving system, by which the precision of particle detection is enhanced.

Figure 4A:
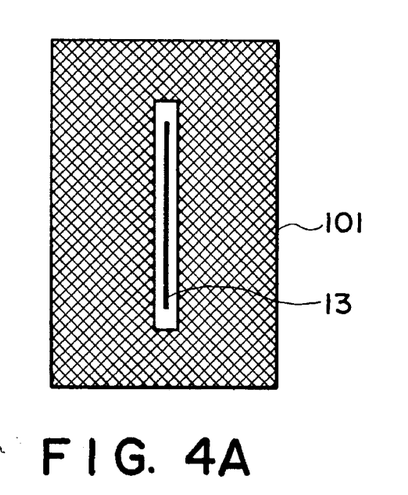
FIGS. 4A and 4B are schematic views, respectively, each for explaining a modified form of the surface state inspecting system as shown in FIGS. 1 and 2.
Figure 4B:
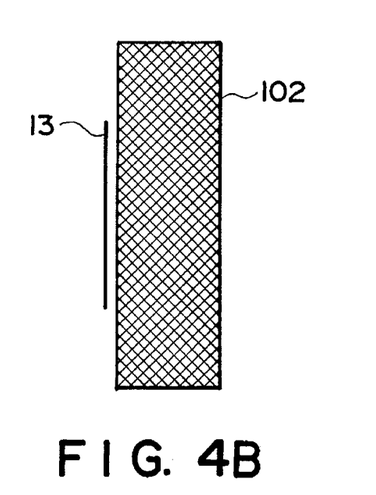

FIGS. 4A and 4B are schematic views for explaining an example where a knife edge is used in place of the field stop 10 of FIGS. 1 and 2. In FIGS. 4A and 4B, denoted at 13 is a region defined adjacent to the field stop 10 position of FIG. 2, and being optically conjugate with the scan region 30a on the reticle 30. While a field stop may use a slit 101 such as shown in FIG. 4A, other than this slit 101 a knife edge 102 such as shown in FIG. 4B may be used. The knife edge 102 shown in FIG. 4B may effectively be used on an occasion when stray light is produced only on one side of the conjugate position 13, such as a case of flare light from a pellicle frame which might be caused when a reticle with a pellicle frame for prevention of particle deposition is inspected.

It is to be noted that, while in the surface state inspecting systems of the embodiments of FIGS. 1–4B embodiments a reticle 6 is moved, the reticle may not be moved and, in place thereof, a structure for two-dimensionally scanning the linearly polarized light $L_V$ may be employed, with a result of a reduction in size of the inspecting system as a whole or a reduction in size of the driving system.

Figure 5:
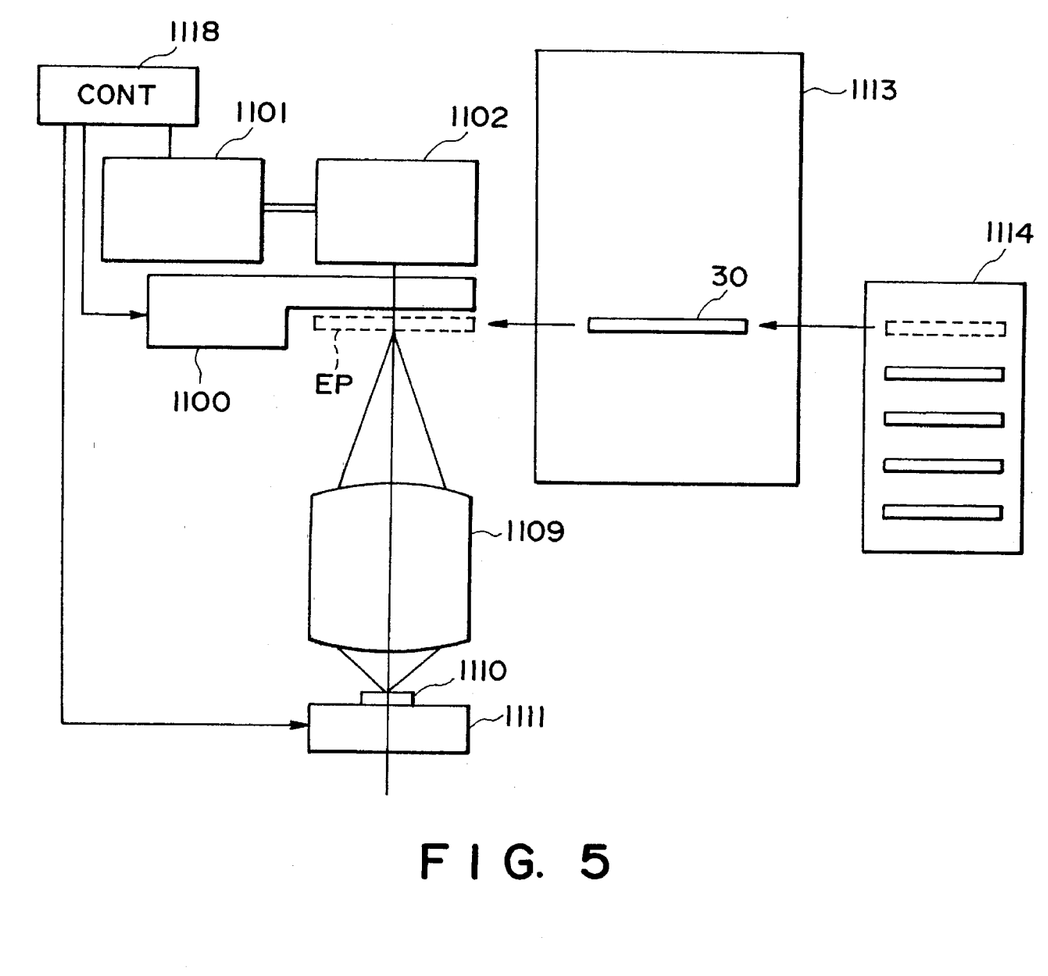
FIG. 5 is a schematic view of an exposure apparatus according to an embodiment of the present invention.

FIG. 5 is a schematic view of an exposure apparatus according to an embodiment of the present invention. In the drawing, denoted at 1100 is an alignment scope, and denoted at 1101 is an ultraviolet light source such as an excimer laser, for example. Denoted at 1102 is an illumination system, and denoted at 1109 is a projection optical system. Denoted at 1110 is a wafer, and denoted at 1111 is a movable stage for holding and moving the wafer 1110. Denoted at 1113 is a particle inspecting system having a structure the same as that of any one of the embodiments described hereinbefore. Denoted at 1114 is a reticle changer, and denoted at 1118 is a controller. The inspecting system 1113 serves to inspect the presence or absence of a particle on a reticle, being taken out from the reticle changer 1114 and being conveyed to the exposure station EP. Since, in the exposure apparatus of this embodiment, only those reticles having no particle deposition are used to perform the exposure process, the reliability is very high.

Now, an embodiment of a device manufacturing method using the projection exposure apparatus of FIG. 5, will be explained below.

Figure 6:
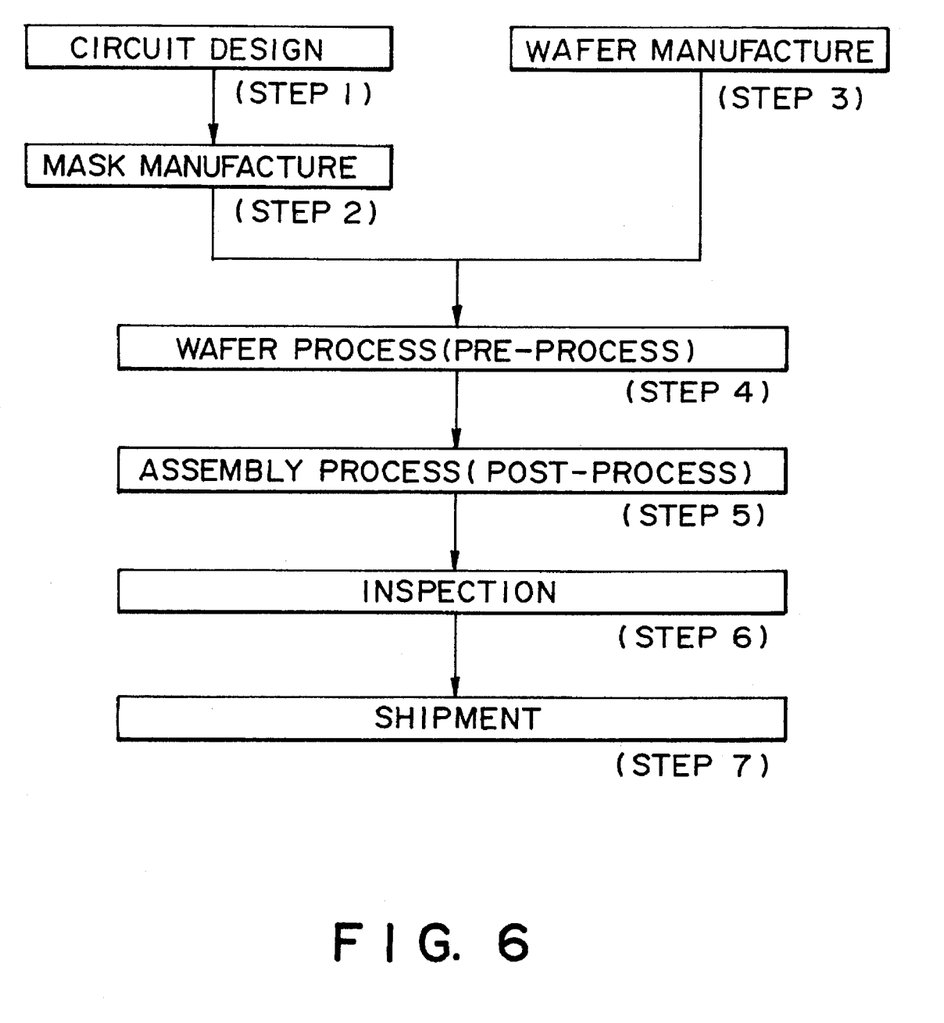
FIG. 6 is a flow chart of semiconductor device manufacturing processes.

FIG. 6 is a flow chart of the sequence of manufacturing a semiconductor device such as a semiconductor chip (e.g., IC or LSI), a liquid crystal panel or a CCD, for example. Step 1 is a design process for designing the circuit of a semiconductor device. Step 2 is a process for manufacturing a mask on the basis of the circuit pattern design. Step 3 is a process for manufacturing a wafer by using a material such as silicon.

Step 4 is a wafer process which is called a pre-process wherein, by using the so prepared mask and wafer, circuits are practically formed on the wafer through lithography. Step 5 subsequent to this is an assembling step which is called a post-process wherein the wafer processed by step 4 is formed into semiconductor chips. This step includes assembling (dicing and bonding) and packaging (chip sealing). Step 6 is an inspection step wherein an operability check, a durability check and so on of the semiconductor devices produced by step 5 are carried out. With these processes, semiconductor devices are finished and they are shipped (step 7).

Figure 7:
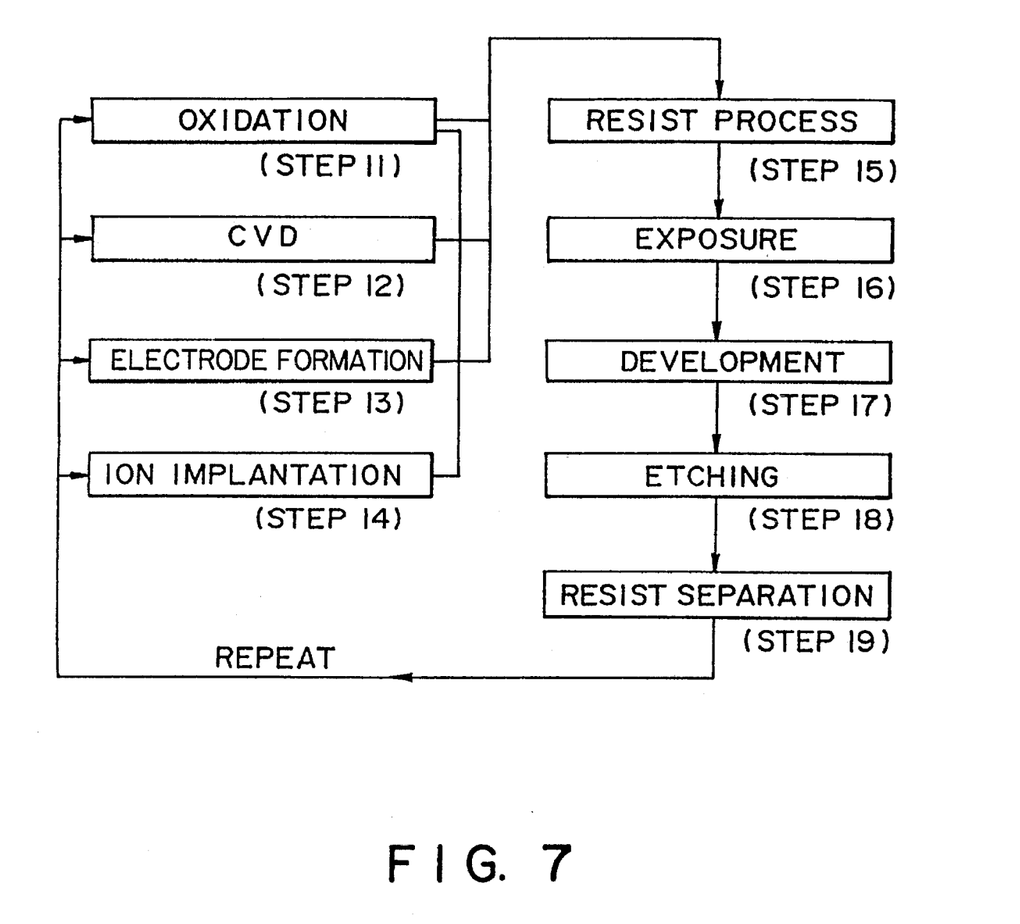
FIG. 7 is a flow chart of a wafer process in the flow chart of FIG. 6.

FIG. 7 is a flow chart showing details of the wafer process. Step 11 is an oxidation process for oxidizing the surface of a wafer. Step 12 is a CVD process for forming an insulating film on the wafer surface. Step 13 is an electrode forming process for forming electrodes on the wafer by vapor deposition. Step 14 is an ion implanting process for implanting ions to the wafer. Step 15 is a resist process for applying a resist (photosensitive material) to the wafer. Step 16 is an exposure process for printing, by exposure, the circuit pattern of the mask on the wafer through the exposure apparatus described above. Step 17 is a developing process for developing the exposed wafer. Step 18 is an etching process for removing portions other than the developed resist image. Step 19 is a resist separation process for separating the resist material remaining on the wafer after being subjected to the etching process. By repeating these processes, circuit patterns are superposedly formed on the wafer.

While the invention has been described with reference to the structures disclosed herein, it is not confined to the details set forth and this application is intended to cover such modifications or changes as may come within the purposes of the improvements or the scope of the following claims.

What is claimed is:

1. A surface state inspecting system, comprising:

a scanning optical system for scanning a surface to be inspected, with first light and simultaneously for scanning a diffraction grating with second light, wherein the first light and the second light have mutually different wavelengths and mutually different polarization directions;

a light receiving optical system for receiving scattered light produced sidewardly from the surface and diffraction light produced sidewardly from the diffraction grating, and for superposing the received lights one upon another; and photoelectric converting means for converting light from said light receiving optical system into an electric signal;

wherein said scanning optical system and said light receiving optical system provide an optical system which is telecentric with respect to the surface to be inspected.

2. A system according to claim 1, wherein said photoelectric converting means has a light receiving surface which is disposed at one of (i) a position of an aperture stop of said light receiving optical system and (ii) a position optically conjugate with the position of the aperture stop of said light receiving optical system.

3. A system according to claim 1, wherein said light receiving optical system includes a field stop disposed at a position optically conjugate with the surface to be inspected.

4. A system according to claim 3, wherein said light receiving optical system further includes a first lens, an aperture stop, a second lens and a field stop disposed in the named order from the surface to be inspected and the diffraction grating, wherein said aperture stop is disposed adjacent to a focal point position of said first lens, and wherein said field stop is disposed at an imaging position of the surface to be inspected, as defined by said first and second lenses.

5. A system according to claim 3, wherein said field stop is disposed with inclination so that it is placed along an imaging plane which satisfies scheimpflug's condition with the surface to be inspected.

6. A system according to claim 1, wherein said scanning optical system includes (i) supplying means for supplying the first and second lights in a state in which the first and second lights are superposed one upon another, (ii) a scanning mirror for scanningly deflecting the superposed first and second lights, (iii) a scanning lens for collecting the first and second lights from said scanning mirror to the surface to be inspected and to the diffraction grating, and (iv) a beam splitter for defining, for the first light, a first light path to the surface to be inspected and for defining, for the second light, a second light path to the diffraction grating.

7. An exposure apparatus, comprising:

a surface state inspecting system for inspecting a surface state of a reticle having a pattern; and means for transferring the pattern of the reticle onto a substrate;

wherein said surface state inspecting system includes (i) a scanning optical system for scanning a surface to be inspected, with first light and simultaneously for scanning a diffraction grating with second light, wherein the first light and the second light have mutually different wavelengths and mutually different polarization directions, (ii) a light receiving optical system for receiving scattered light produced sidewardly from the surface and diffraction light produced sidewardly from the diffraction grating, and for superposing the received lights one upon another, and (iii) photoelectric converting means for converting light from said light receiving optical system into an electric signal, wherein said scanning optical system and said light receiving optical system provide an optical system which is telecentric with respect to the surface to be inspected.

8. A device manufacturing method usable with a reticle having a device pattern, said method comprising the steps of:

scanning, through a scanning optical system, a surface of the reticle to be inspected, with first light and simultaneously scanning a diffraction grating with second light, wherein the first light and the second light have mutually different wavelengths and mutually different polarization directions;

receiving, through a light receiving optical system, scattered light produced sidewardly from the surface and diffraction light produced sidewardly from the diffraction grating, and superposing the received lights one upon another, wherein the scanning optical system and the light receiving optical system provide an optical system which is telecentric with respect to the surface to be inspected;

converting light from the light receiving optical system into an electric signal, and inspecting the surface to be inspected, on the basis of the electric signal; and transferring the device pattern of the surface inspected reticle onto a wafer.

\* \* \* \* \*

UNITED STATES PATENT AND TRADEMARK OFFICE
CERTIFICATE OF CORRECTION

PATENT NO. : 5,591,985
DATED : January 7, 1997
INVENTOR(S) : Toshihiko TSUJI, et al.

It is certified that error appears in the above-indentified patent and that said Letters Patent is hereby corrected as shown below:

COLUMN 2:

Line 36, "scheimpflug's" should read --Scheimpflug's--.

COLUMN 4:

Line 31, "Published" should read --published--; and
Line 57, "Pub-" should read --pub- --.

COLUMN 5:

Line 51, "tens" should read --lens--; and
Line 61, "goes" should read --go--.

COLUMN 6:

Line 49, "scheimpflug's" should read --Scheimpflug's--.

UNITED STATES PATENT AND TRADEMARK OFFICE
CERTIFICATE OF CORRECTION

PATENT NO. : 5,591,985
DATED : January 7, 1997
INVENTOR(S) : Toshihiko TSUJI, et al.

It is certified that error appears in the above-indentified patent and that said Letters Patent is hereby corrected as shown below:

COLUMN 7:

Line 32, "embodiments" should be deleted; and
Line 46, "havinga" should read --having a--.

COLUMN 9:

Line 10, "scheimpflug's" should read --Scheimpflug's--.

Signed and Sealed this

Fifteenth Day of July, 1997

Attest:

BRUCE LEHMAN

Attesting Officer                Commissioner of Patents and Trademarks